(12) United States Patent
Kim et al.

(10) Patent No.: US 11,912,690 B2
(45) Date of Patent: *Feb. 27, 2024

(54) ACID ADDITION SALTS OF BENZIMIDAZOLE DERIVATIVE

(71) Applicant: HK INNO.N CORPORATION, Chungcheongbuk-do (KR)

(72) Inventors: Eun Sun Kim, Gangwon-do (KR); Min Kyoung Lee, Seoul (KR); Sung Ah Lee, Gyeonggi-do (KR); Kwang Do Choi, Gyeonggi-do (KR); Jae Sun Kim, Gyeonggi-do (KR); Hyung Chul Yoo, Gyeonggi-do (KR)

(73) Assignee: HK INNO.N CORPORATION, Chungcheongbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,806

(22) Filed: Nov. 21, 2022

(65) Prior Publication Data

US 2023/0192670 A1  Jun. 22, 2023

Related U.S. Application Data

(63) Continuation of application No. 16/334,427, filed as application No. PCT/KR2017/010332 on Sep. 20, 2017, now Pat. No. 11,535,610.

(30) Foreign Application Priority Data

Sep. 21, 2016 (KR) .................. 10-2016-0120996

(51) Int. Cl.
  *C07D 405/12* (2006.01)
  *C07D 235/06* (2006.01)

(52) U.S. Cl.
  CPC ......... *C07D 405/12* (2013.01); *C07D 235/06* (2013.01)

(58) Field of Classification Search
  CPC ..... A61K 31/4184; A61K 9/0019; A61P 1/04; C07D 235/06; C07D 405/12
  See application file for complete search history.

(56) References Cited

U.S. PATENT DOCUMENTS

| | | | |
|---|---|---|---|
| 7,718,809 B2 | 5/2010 | Koike et al. | |
| 7,723,321 B2 | 5/2010 | Hanazawa et al. | |
| 8,648,080 B2 | 2/2014 | Takahashi et al. | |
| 2007/0142448 A1 | 6/2007 | Hanazawa et al. | |
| 2008/0200479 A1 | 8/2008 | Biondi et al. | |
| 2008/0214519 A1 | 9/2008 | Koike et al. | |
| 2012/0035212 A1 | 2/2012 | Brown et al. | |
| 2012/0115820 A1 | 5/2012 | Takahashi et al. | |

FOREIGN PATENT DOCUMENTS

| | | | |
|---|---|---|---|
| CN | 101341149 | 1/2009 | |
| CN | 101341149 | 6/2011 | |
| KR | 10-2008-0080195 | 9/2008 | |
| KR | 10-2011-0038011 | 4/2011 | |
| KR | 10-2012-0052269 | 5/2012 | |
| TW | 200732326 | 9/2007 | |
| WO | 2005042485 | 5/2005 | |
| WO | 2006134460 | 12/2006 | |
| WO | 2007072146 | 6/2007 | |
| WO | WO-2007072146 A1 * | 6/2007 | ......... A61K 31/4184 |
| WO | 2010000469 | 1/2010 | |
| WO | 2016117814 | 7/2016 | |
| WO | 2019009661 | 1/2019 | |

OTHER PUBLICATIONS

International Preliminary Report on Patentability dated Mar. 19, 2019 in International Application No. PCT/KR2017/010332.
Extended European Search Report dated Apr. 22, 2020 in corresponding European Patent App. No. 17853411.1.
Bastin et al. in Organic Process Research & Development 2000, 4, 427-435 (Year: 2000).
Murdande et al. in Pharmaceutical Development and Technology, 2011; 16(3): 187-200 (Year: 2011).

\* cited by examiner

*Primary Examiner* — Jean P Cornet
(74) *Attorney, Agent, or Firm* — Giordano Law LLC; David A. Giordano

(57) ABSTRACT

The present invention relates to a pidolate salt and malate salt of a compound represented by a formula 1 with an excellent liquid-phase stability, solid-phase stability, water solubility, precipitation stability and hygroscopicity all together as a compound for preventing and treating diseases mediated by an acid pump antagonistic activity, as well as a method for preparing the same.

20 Claims, 8 Drawing Sheets

ACID ADDITION SALTS OF BENZIMIDAZOLE DERIVATIVE

TECHNICAL FIELD

The present invention relates to acid addition salts of a benzimidazole derivative with an excellent stability and solubility as well as a method for preparing the same.

BACKGROUND

4-[((4S)-5,7-difluoro-3,4-dihydro-2H-chromen-4-yl) oxy]-N,N,2-trimethyl-1H-benzimidazole-6-carboxamide [(S)-4-((5,7-difluorochroman-4-yl)oxy)-N,N,2-trimethyl-1H-benzo[d]imidazole-6-carboxamide] represented by a following formula 1 is a pharmaceutically active component having a molecular weight of 387.39:

[Formula 1]

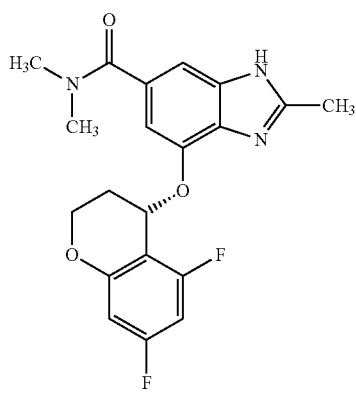

This compound is a pharmaceutical ingredient for preventing and treating diseases mediated by an acid pump antagonistic activity, including (but not limited to) gastrointestinal diseases, for example, a gastroesophageal disease, a gastroesophageal reflux disease (GERD), a peptic ulcer, a gastric ulcer and a duodenal ulcer, an ulcer induced by NSAID, a gastritis, a *Helicobacter pylori* infection, a dyspepsia and a functional dyspepsia, a Zollinger-Ellison syndrome, a nonerosive reflux disease (NERD), a visceral pain, a purosis, a nausea, an esophagitis, a dysphagia, a salivation, an airway lesion and an asthma.

International Patent No. WO2007072146 discloses benzimidazole derivatives substituted with a chromane, acting as an acid pump inhibitor ($H^+$ $K^+$ ATPase inhibitor). Also, International Patent No. WO2016117814 discloses a novel crystal form of the above-mentioned formula 1 and a method for preparing the same. In particular, the patent discloses a crystalline free base of a compound of the above-mentioned formula 1, which is advantageous for preparing a formulation because of being stable under a long-term and stress storage condition, having no crystal transition observed due to a change with the passage of time, having an excellent photostability, and having a low hygroscopicity and a low induction of static electricity.

The above-mentioned compound has a limitation to selection of salts because the compound has a very low water solubility (0.02 mg/ml, pH 6.8), has a solubility increased (0.7 mg/ml, pH 3.0) under an acidic condition, but without a great effect, and has a degradation product increased under an acidic condition, such that the compound does not have a good stability. Also, in case of using a solubilizing agent, such as a surfactant, to improve solubility, excessive amounts of excipients are needed, thus causing a difficulty.

Meanwhile, a free base or crystalline acid addition salts cannot secure significant water solubility in terms of a formulation. In particular, when considering an injection formulation, it is necessary to secure precipitation stability in addition to a dissolution rate so that a precipitation thereof cannot occur in a plasma pH. Therefore, it is important to sufficiently secure both kinetic and thermodynamic solubility. However, amorphous acid addition salts are very difficult to secure both solubility and stability due to characteristics of the compound, which has a low thermodynamic solubility and degrades under an acidic condition at the same time.

In light of pharmaceuticals, a polymorphic crystal form is important because the polymorphic crystal form may exist in a variety of forms depending on drugs and a specific polymorphic crystal form may have an influence on easiness of preparing a pharmaceutical ingredient, solubility, storage stability, easiness of preparing a completed drug product, and pharmaceutical activity in vivo. A criterion for selecting an excellent crystal form is based on the most important physicochemical characteristics required by a drug, and selection of an optimized crystal form may vary depending on purposes, for example, for choosing a thermodynamically most stable one, for choosing a pharmaceutically optimized one for a pharmaceutical ingredient and a completed drug product, for improving a solubility and dissolution rate of a drug, or for bringing about a change in pharmacokinetic characteristics.

Meanwhile, in case of an amorphous pharmaceutical ingredient, a surface area of a particle increases, so a kinetic solubility generally increases, but there is still a limitation to improving a thermodynamic solubility under an in vivo pH condition. Furthermore, the amorphous pharmaceutical ingredient does not have a lattice energy caused by crystallization, does not have a distinct melting point, and has a remarkably low stability in comparison with an identical crystalline one. Meanwhile, when pharmaceutically preparing an injection formulation, the amorphous pharmaceutical ingredient is often used as a solid capable of being prepared into a lyophilized material. In this case, however, the amorphous pharmaceutical ingredient must secure stability within a preparation thereof, as well as solubility and precipitation stability all together.

Accordingly, the present inventors have made efforts to develop acid addition salts, which can be used as a pharmaceutical ingredient for a thermodynamically very stable injection preparation, while a compound represented by the above-mentioned formula 1 has excellent water solubility and precipitation stability at the same time. In result, it was identified that a pidolate salt and malate salt of the compound represented by the formula 1 had excellent stability and solubility at the same time, thus completing the present invention.

PRIOR ART REFERENCES

Patent Documents

International Patent No. WO2007072146
International Patent No. WO2016117814

DETAILED DESCRIPTION OF THE INVENTION

Technical Problem

The objective of the present invention is to provide a pidolate salt or malate salt of a compound represented by a following formula 1 as well as a method for preparing the same.

[Formula 1]

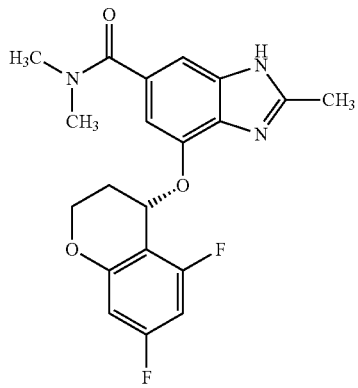

Technical Solution in one aspect for solving the aforementioned task, the present invention provides a pidolate salt or malate salt of a compound represented by a following formula 1.

[Formula 1]

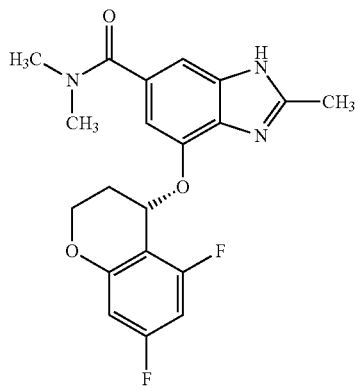

Specifically, the pidolate salt of the compound of the formula 1 may be a pidolate salt represented by a following formula 2, and the malate salt of the compound of the formula 1 may be a malate salt represented by a following formula 3.

[Formula 2]

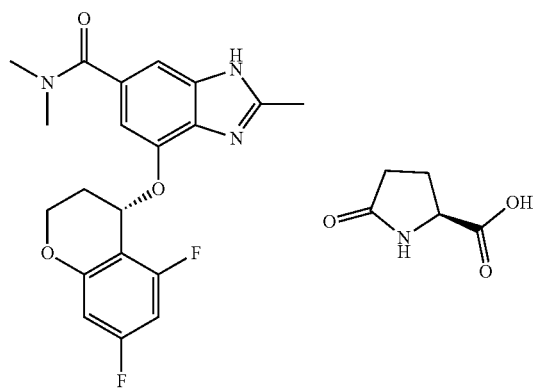

[Formula 3]

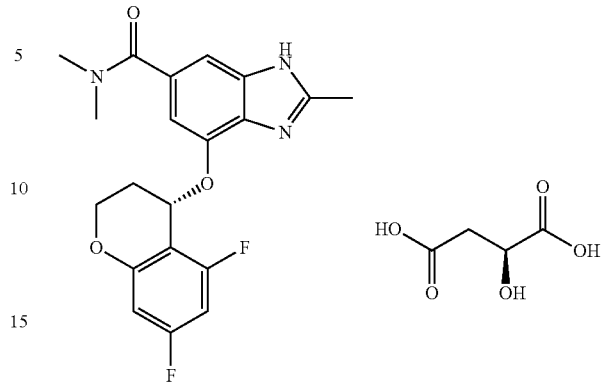

In the present invention, the compound of the formula 1 is a novel material for preventing and treating gastrointestinal diseases and bleeding related to the same according to a pharmacological mechanism of a potassium competitive acid blocker (P-CAB). The compound of the formula 1 has solubility of just 0.02 mg/ml in a buffer solution of pH 6.8, thus having very low water solubility under an in vivo pH condition. In addition, a degradation product of a following formula 4 continues to increase proportionately to an exposure time in an acidic environment in which solubility increases.

[Formula 4]

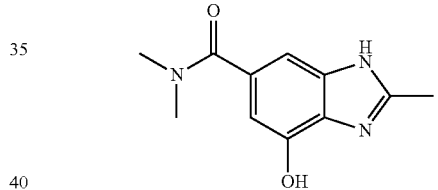

Specifically, the degradation product of the formula 4 is generated as an ether linkage is disconnected under an acidic condition by means of a mechanism of a following formula 5, and the degradation product tends to increase proportionately, as a pH gets lower or an exposure time gets longer in a low pH.

[Formula 5]

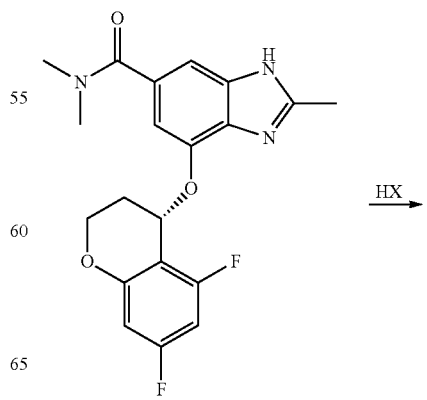

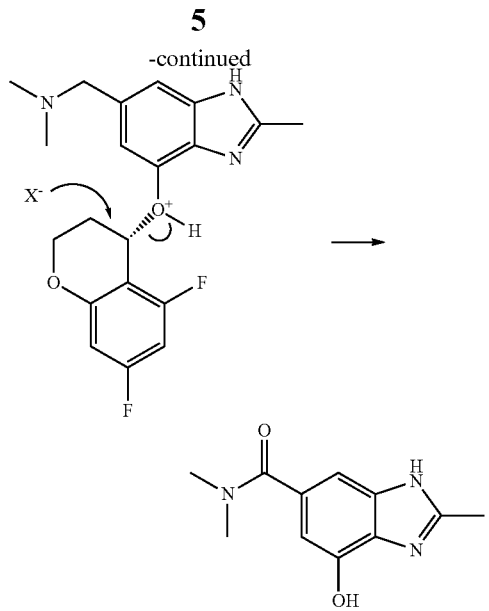

A water solubility of the compound of the formula 1 is only 0.7 mg/ml under the condition of a buffer solution of pH 3, such that a much lower pH is required to increase the solubility. In this case, however, there is a difficulty in maintaining stability. In addition, even if the solubility is improved in a low pH, precipitation must not occur under the condition of an in vivo pH, such that a physical property of the compound of the formula 1, as required in the present invention, must satisfy following four conditions at the same time:

1) preferably securing solubility of so mg/ml or more, when considering a dose and volume; 2) having no degradation product precipitated even with passage of time in the state that at least to mg/ml thereof is dissolved in a buffer solution of pH 6.8; 3) securing stability enough to be used as a pharmaceutical ingredient; and 4) maintaining amorphousness during storage and not being converted into crystalline due to a change with the passage of time.

The present inventors intended to prepare a co-crystal between the compound of the formula 1 and a water-soluble amino acid in order to satisfy the above-mentioned four conditions. In this regard, European Patent Publication No. EP2493457 discloses a solid composite, which is fast dissolved in such a way that an amino acid is bound with a drug as a matrix forming agent. Therefore, the compound of the formula 1 of the present invention must not be precipitated under an in vivo pH condition while being eluted fast at the same time. However, in case of bringing about a fast elution by lowering a pH like an acid addition salt, a degree of ionization is dropped in an in vivo pH environment, which is close to neutral, such that there may be a possibility of inducing solid precipitation. Therefore, the present inventors made an attempt to prepare a co-crystal by a medium of an intermolecular bonding as well as a hydrogen bonding between a water-soluble amino acid and the compound of the formula 1 so as to be relatively less influenced by pH.

A following table 1 shows amino adds used as a co-crystal former in the present invention as well as a compound capable of forming a co-crystal, and an equivalent weight of the co-crystal former was set to 1:1 molar ratio compared to the compound of the formula 1.

TABLE 1

| No. | Co-crystal formers consisting of amino acids and the like |
|---|---|
| 1 | L-Lysine |
| 2 | L-Cysteine |
| 3 | L-Valine |
| 4 | L-Phenylalanine |
| 5 | Creatine |
| 6 | L-Alanine |
| 7 | L-Arginine |
| 8 | Vanillin |
| 9 | Glycine |
| 10 | L-Hydroxyproline |
| 11 | L-isoleucine |
| 12 | L-leucine |

A following table 2 indicates a crystallizability and water solubility at a room temperature when forming a co-crystal at a 1:1 molar ratio between a co-crystal former of the table 1 and the compound of the formula 1. Specifically, co-crystal formers of. Nos. 1 to 6 in the table 1 formed a crystalline one, and co-crystal formers of Nos. 7 to 12 indicated noncrystalline characteristics, wherein results thereof were identified through a PXRD. Meanwhile, as an example of a crystalline one, a co-crystal between the compound of the formula 1 and L-Alanine can indicate crystalline characteristics by a medium of a hydrogen bonding as shown in a following formula 6.

[Formula 6]

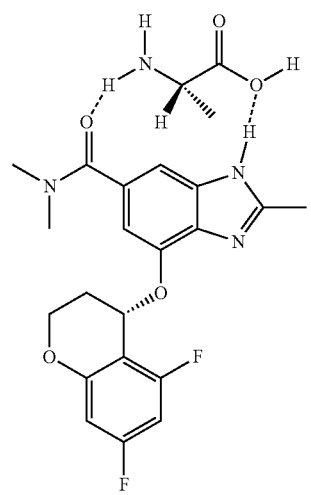

TABLE 2

| No. | Co-crystal former | Crystallizability | Water-solubility (mg/ml) |
|---|---|---|---|
| 1 | L-Lysine | Crystalline | 8 |
| 2 | L-Cysteine | Crystalline | 1 |
| 3 | L-Valine | Crystalline | 3 |
| 4 | L-Phenylalanine | Crystalline | 0.5 |
| 5 | Creatine | Crystalline | 1 |
| 6 | L-Alanine | Crystalline | 4 |
| 7 | L-Arginine | Noncrystalline | 11 |
| 8 | Vanillin | Noncrystalline | 9 |
| 9 | Glycine | Noncrystalline | 5 |
| 10 | L-Hydroxyproline | Noncrystalline | 10 |
| 11 | L-isoleucine | Noncrystalline | 13 |
| 12 | L-leucine | Noncrystalline | 12 |

Based on results of the table 2, it was identified that the compound of the formula 1 in the present invention did not have water-solubility greatly improved upon being reaction-bonded with a co-crystal former consisting of a group of related compounds having a water-soluble amino acid and a hydrogen bond donor and receptor. However, it was identified that a noncrystalline solid had a relatively higher degree of improvement in solubility compared to a crystalline solid, such that the present invention came to completion based on the above-mentioned results.

According to the present invention, salts satisfying all the above-mentioned conditions are a pidolate salt of the compound of the formula 1 and a malate salt of the compound of the formula 1.

Specifically, the pidolate salt of the compound of the formula 1, represented by the formula 2, is formed in such a way that the compound of the formula 1 and a pyroglutamic acid form a salt, and the pyroglutamic acid can be used to have the same meaning as a pyroglutamate, a pidolic acid or a pidolate. Specifically, the pyroglutamic acid may be an L-pyroglutamic acid.

Also, the malate salt of the compound of the formula 1, represented by the formula 3, is formed in such a way that the compound of the formula 1 and a malic acid form a salt, and the malic acid can be used to have the same meaning as a malate. Specifically, the malic acid may be an L-malic acid.

The pidolate salt of the compound of the formula 1 or the malate salt of the compound of the formula 1 may be preferably noncrystalline or partially crystalline, and most preferably partially crystalline in which at least 95 wt % based on the total wt % of salt is noncrystalline.

In one exemplary embodiment of the present invention, as a result of comparing solubility of 12 types of amorphous acid addition salt of the compound of the formula 1, fumaric, oxalic, citric, L-pyroglutamic, L-malic and L-tartaric acid salts showed a more excellent solubility compared to other salts (Table 4). Out of the six types of salt, it was identified that L-pyroglutamic and L-malic acid salts showed a more excellent liquid-phase stability and solid-phase stability compared to other salts (Tables 5 and 6) and maintained a homogeneous solution even under the condition of an in vivo pH 6.8 (Table 7), so it could be seen that the pidolate of the compound of the formula 1 and the malate salt of the compound of the formula 1 were a pharmaceutical ingredient for a preparation optimized for the compound of the formula 1.

In another aspect, the present invention provides a pharmaceutical composition for preventing or treating diseases mediated by an acid pump antagonistic activity including a pidolate salt or malate salt of the compound of the formula 1.

The pidolate salt of the compound of the formula 1 and the malate salt of the compound of the formula 1 are such as that described above.

The diseases mediated by an acid pump antagonistic activity may be one selected from the group consisting of a gastroesophageal disease, a gastroesophageal reflux disease (GERD), a peptic ulcer, a gastric ulcer and a duodenal ulcer, an ulcer induced by NSAID, a gastritis, a *Helicobacter pylori* infection, a dyspepsia and a functional dyspepsia, a Zollinger-Ellison syndrome, a nonerosive reflux disease (NERD), a visceral pain, a purosis, a nausea, an esophagitis, a dysphagia, a salivation, an airway lesion and an asthma.

A pharmaceutical composition of the present invention may be one formulation selected from the group consisting of powder, granule, tablet, capsule, suspension, emulsion, syrup, aerosol, ointment, cream, suppository and injection, but not limited thereto. Specifically, the pharmaceutical composition may be an injection formulation due to characteristics of the pidolate or malate salt of the compound of the formula 1, represented by the formula 2 or 3, contained in the pharmaceutical composition of the present invention, in that the pidolate or malate salt show excellent stability in an in vivo pH environment.

An amount of an active component contained in a composition of the present invention varies depending on a state of a patient to be administered, a targeted degree of treatment, etc. Preferably, the composition of the present invention may contain the compound of the formula 1 present as an active component in the compound represented by the formula 2 or the compound represented by the formula 3 at a concentration of 1 to 100 mg/ml, preferably 1 to 50 mg/ml. If the active component is contained at a low concentration of 1 mg/ml or less, a large dose of injection may be administered to exhibit a sufficient therapeutic effect, thus causing a difficulty with administration to an affected area of a patient. On the other hand, if the active component is contained at a high concentration of 100 mg/ml or more, it may be difficult to satisfy a composition that dissolves even a stabilizer while an impurity may occur or precipitation may be generated upon resuspension or dissolution.

When preparing an injection composition according to the present invention, water for injection may be used to prepare the same. According to the present invention, an injection containing a pharmaceutically acceptable salt of the compound of the formula 1 may selectively comprise an isotonic agent, a buffer solution, an osmotic agent, etc., which are conventionally used in the art, but not limited thereto.

Also, the present invention provides a use of a pidolate salt or malate salt of the compound represented by the formula 1 so as to be used to prevent or treat diseases mediated by an acid pump antagonistic activity.

Furthermore, the present invention provides a use of a pidolate salt or malate salt of the compound represented by the formula 1 so as to be used to prepare a medicine for preventing or treating diseases mediated by an acid pump antagonistic activity. The pidolate salt or malate salt represented by the compound represented by the formula 1 for preparing a medicine may be mixed with an acceptable adjuvant, a diluent, a carrier, etc., and may be prepared as a composite preparation along with other active agent, thus bringing about a synergy effect on active components.

Moreover, the present invention provides a method for preventing or treating diseases mediated by an acid pump antagonistic activity, comprising: administering a therapeutically effective amount of a pidolate salt or malate salt of the compound represented by the formula 1.

According to the present invention, the above-mentioned "object" comprises mammals, in particular, humans.

A term of a "therapeutically effective amount" used in the present invention means such an effective amount of the salt as to prevent or treat diseases mediated by an acid pump antagonistic activity.

According to the present invention, a method for preventing or treating diseases mediated by an acid pump antagonistic activity comprises: administering the above-mentioned salts, thereby dealing with the diseases themselves before expression of symptoms thereof as well as inhibiting or avoiding such symptoms. In managing diseases, a preventive or therapeutic dosage of a specific active component varies depending on a nature and severity of the disease or a state thereof, as well as a path through which the active component is administered. A dosage and a frequency thereof vary depending on an individual patient's age, weight and response. An appropriate dosing regimen may be easily selected by those skilled in the art that considers these factors of course.

The matters mentioned in the use, composition, and methods of treatment of the present invention act on identically unless they contradict to each other.

In yet another aspect, the present invention provides a method for preparing a pyroglutamate salt or malate salt of a compound represented by a formula 1, wherein the method comprises:
a) dissolving a compound represented by a formula 1 and a pyroglutamic acid or a malic acid as an acid addition salt in an organic solvent;
b) concentrating a solution prepared in the step a) under decompression to precipitate a solid and then adding a co-solvent thereto to stir a resulting solution; and
c) filtering out and drying a precipitated solid.

More specifically, the preparing method of the present invention comprises: the step a) of dissolving the compound represented by the formula 1 in the organic solvent and dissolving the acid addition salt therein. At this time, the acid used above is a pyroglutamic acid or a malic acid. If other acids are used to prepare the acid addition salt and dissolve the same, the prepared salt of the compound of the formula 1 has a low liquid-phase or solid-phase stability, for example, by not improving solubility or by generating a degradation product or an impurity, and may cause a problem, for example, by precipitating a solid.

Specifically, the pyroglutamic acid may be an L-pyroglutamic acid, and the malic acid may be an L-malic acid.

The organic solvent may be a methanol, but not limited thereto, wherein the organic solvent may be added by 5 to 20 times (volume/weight), preferably to times (volume/weight) compared to a compound represented by the formula 1. If an addition amount of the organic solvent is less than 5 times or more than 20 times of the compound represented by the formula 1, an amount of pidolate or malate contained in the salt prepared may not be appropriate to exhibit an excellent solubility and stability.

More specifically, the preparing method of the present invention comprises: concentrating a solution prepared in the step a) under decompression to precipitate a solid and then adding a co-solvent thereto to stir a resulting solution.

The co-solvent may be a mixed solvent of acetone and ethyl acetate, but not limited thereto, wherein the co-solvent may be added by 1 to 10 times (volume/weight), preferably 5 times (volume/weight) compared to a compound represented by the formula 1. If an addition amount of the organic solvent is less than 1 time or more than 10 times of the compound represented by the formula 1, an amount of pidolate or malate contained in the salt prepared may not be appropriate to exhibit an excellent solubility and stability.

A ratio of the co-solvent between acetone and ethyl acetate may be acetone:ethyl acetate=1:4 (V/V), but not limited thereto.

More specifically, the preparing method of the present invention comprises: filtering out and drying a solid precipitated in the step b).

The filtering may be a decompression filtration, but not limited thereto.

The drying may be performed by means of a conventional drying method, for example, freeze-drying, rotary evaporation drying, spray drying, vacuum drying or fluid-bed drying, specifically vacuum drying.

Advantageous Effects

Novel amorphous acid addition salts of a compound of a formula 1 provided in the present invention can be easily used as a pharmaceutical ingredient for an oral preparation and injection preparation because of having excellent physicochemical characteristics, stability and solubility all together.

MODE FOR INVENTION

Hereinafter, configuration and effects of the present invention will be described in more detail in light of the following Examples which are set forth to illustrate, but are not to be construed to limit the present invention.

Example 1: Preparing of a Pidolate Salt of a Compound of a Formula 1

Figure 1:
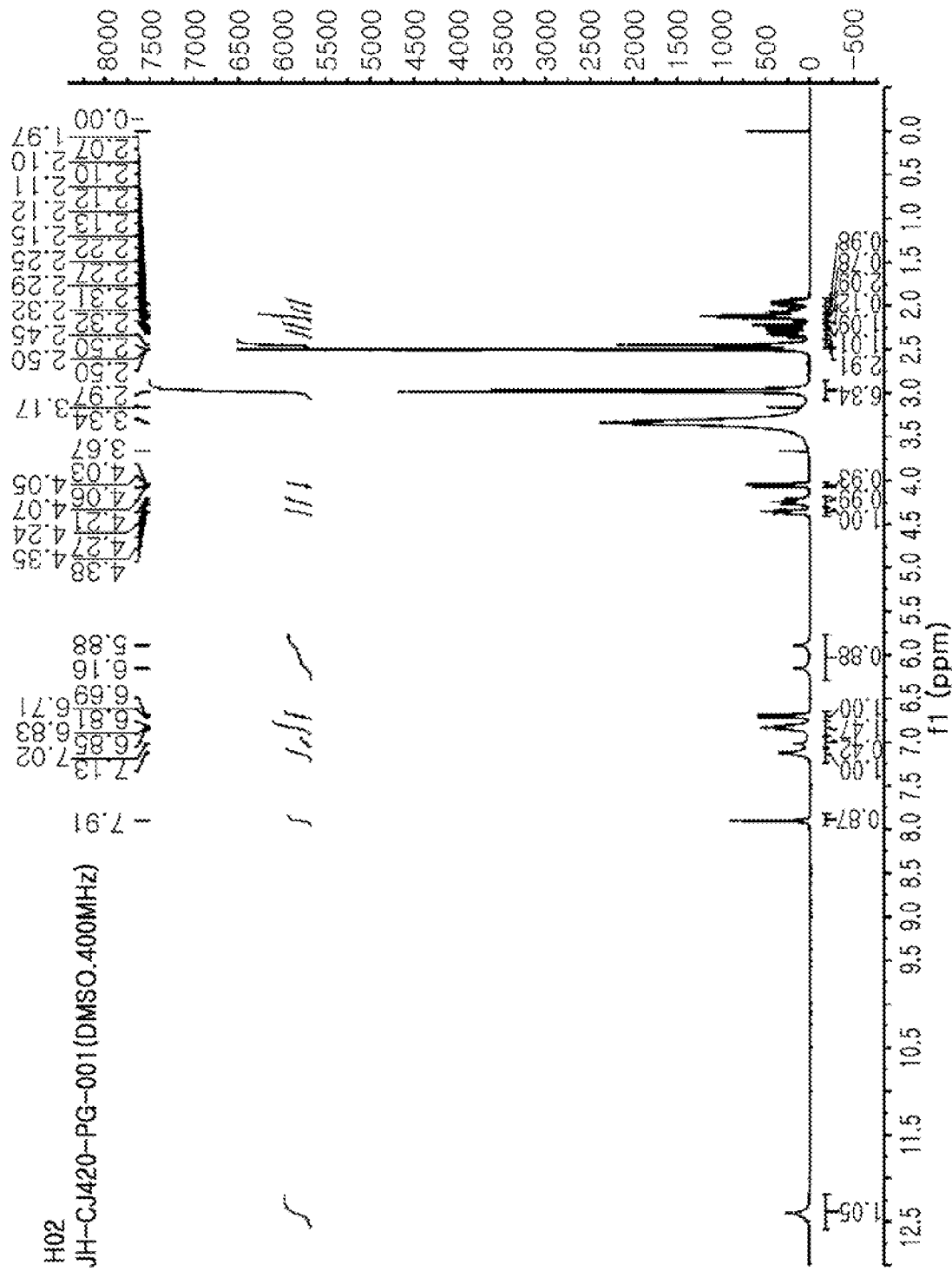
FIG. 1 shows a $^1$H-NMR results of a pidolate salt of an amorphous compound of a formula 1, prepared according to an embodiment of the present invention.

A 100 g of a crystalline compound of a formula 1 and 34.98 g of L-pyroglutamic acid (1.05 eq.) were completely dissolved in 1000 ml of methanol at 25° C., and then a resulting solution was concentrated at 5° C. while being stirred under decompression until a solid was precipitated. A co-solvent of acetone and ethyl acetate was added to a concentrate at 25° C. at a ratio of acetone:ethyl acetate=1:4 (500 ml), and a resulting solution was stirred agitatedly for 30 minutes. The solid was filtered out under decompression, washed with 100 ml of ethyl acetate, and vacuum-dried at 40° C. for 16 hours, such that a pidolate salt of an amorphous compound of the formula 1 was obtained by 113.8 g (yield 85.4%) in a form of white powder (FIG. 1).

Example 2: Preparing of a Malate Salt of a Compound of a Formula 1

Figure 2:
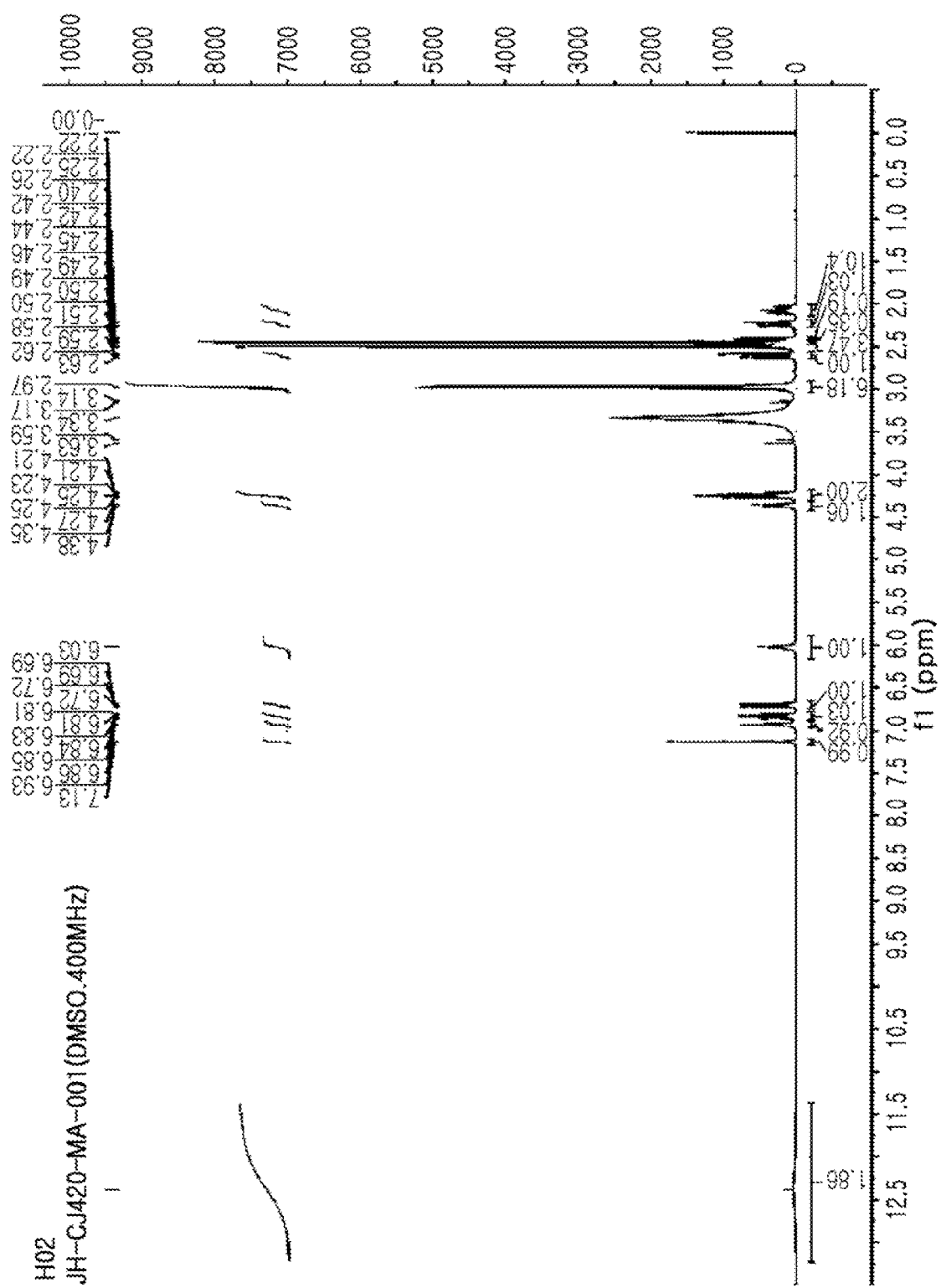
FIG. 2 shows a $^1$H-NMR results of a malate salt of an amorphous compound of the formula 1, prepared according to an embodiment of the present invention.
Figure 3:
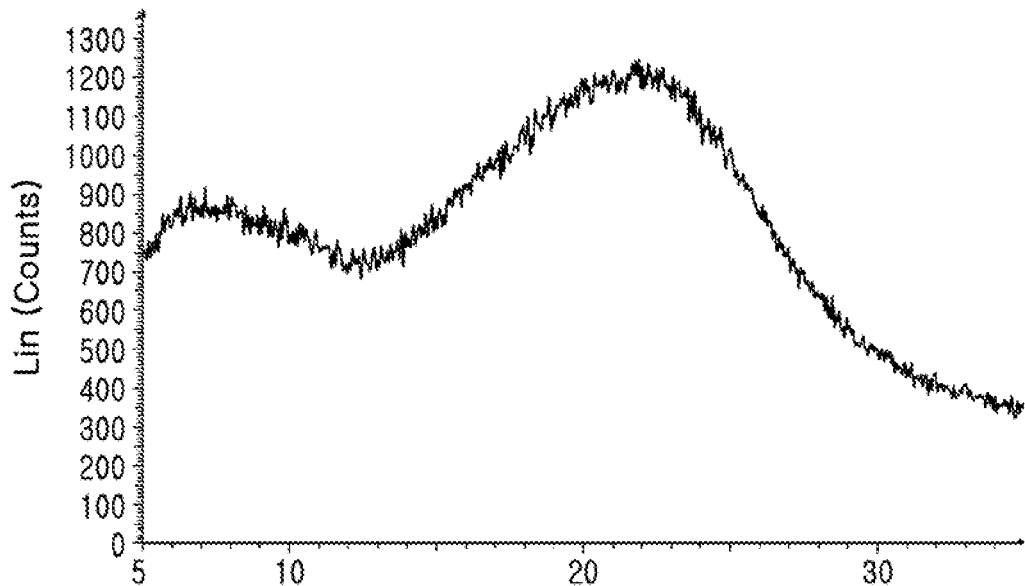
FIG. 3 shows a PXRD results of a pidolate salt of an amorphous compound of the formula 1, prepared according to an embodiment of the present invention.
Figure 4:
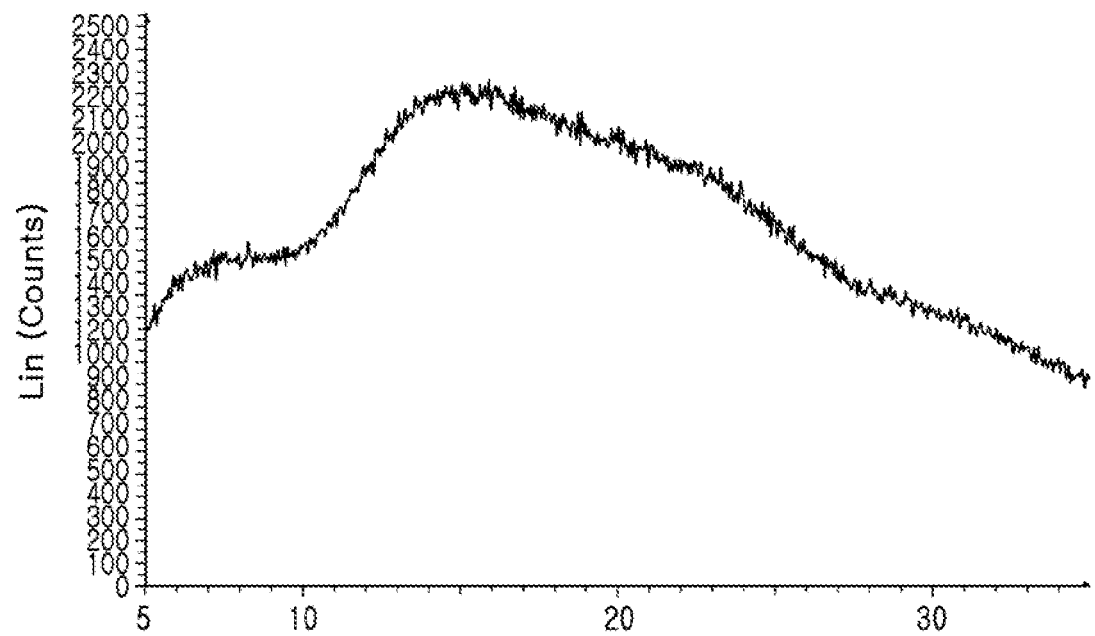
FIG. 4 shows a PXRD results of a malate salt of an amorphous compound of the formula 1, prepared according to an embodiment of the present invention.
Figure 5:
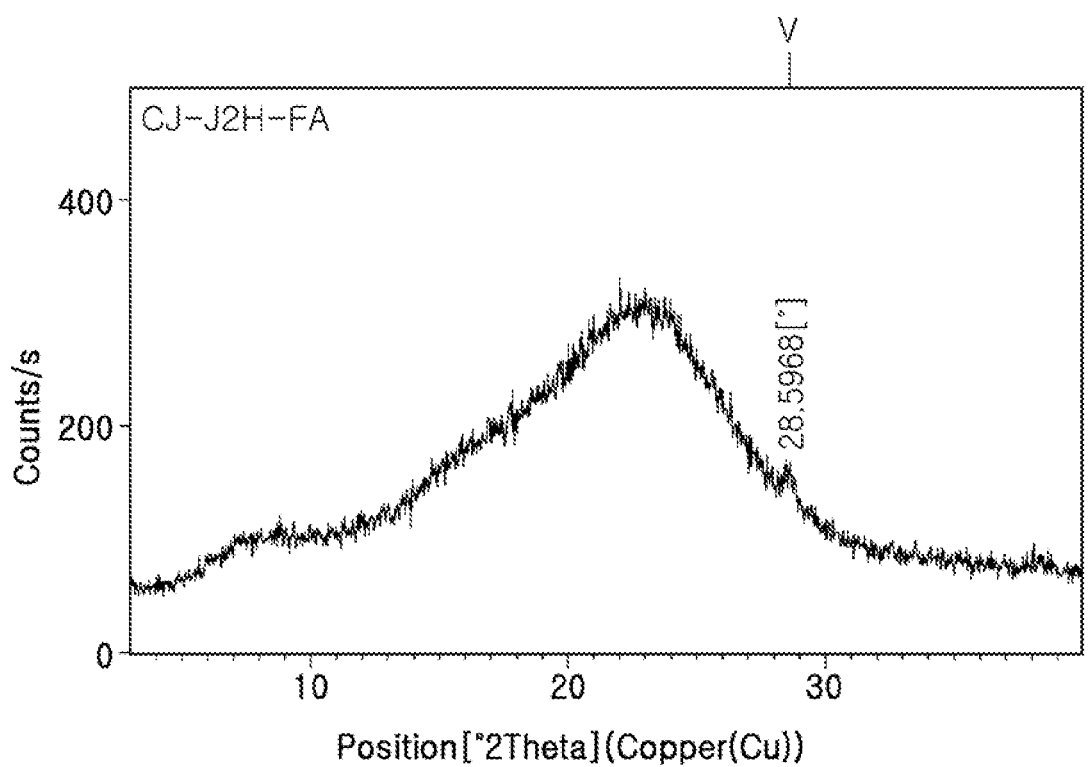
FIG. 5 shows a PXRD results of a fumaric acid salt of an amorphous compound of the formula 1, prepared according to an embodiment of the present invention.
Figure 6:
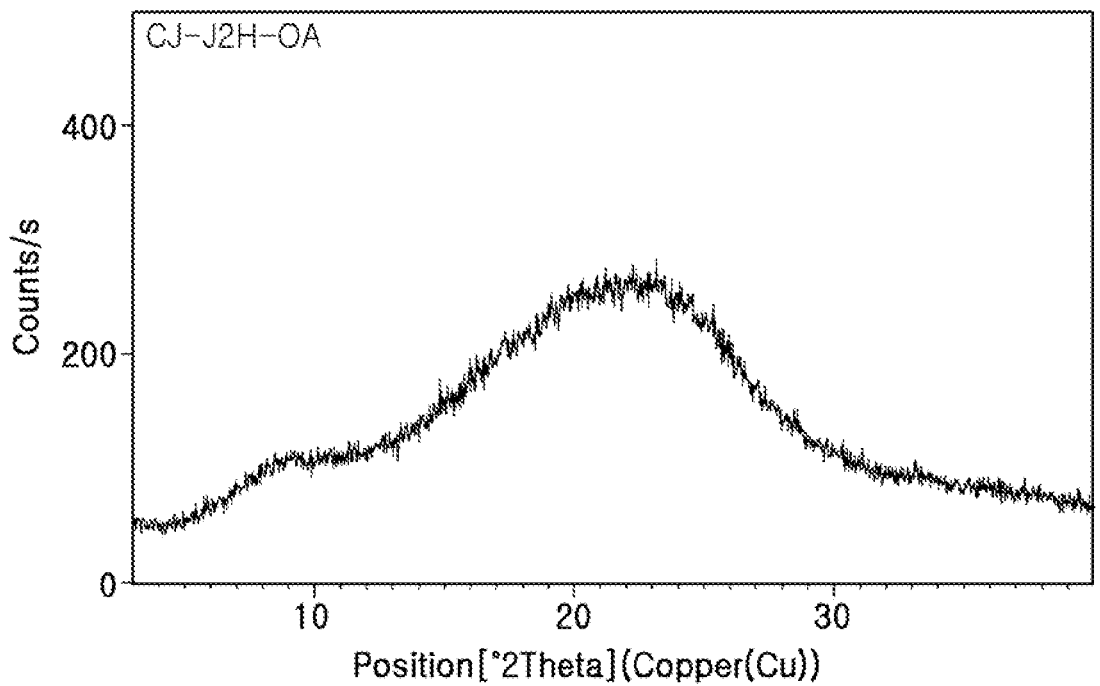
FIG. 6 shows a PXRD results of an oxalic acid salt of an amorphous compound of the formula 1, prepared according to an embodiment of the present invention.
Figure 7:
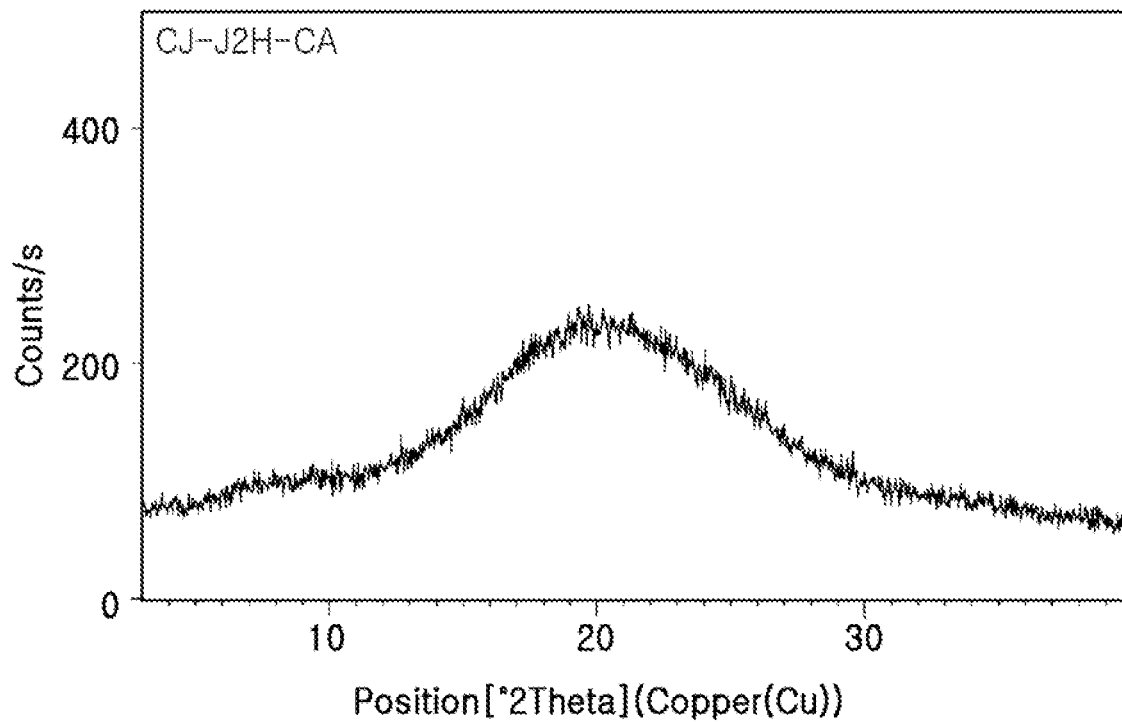
FIG. 7 shows a PXRD results of a citric acid salt of an amorphous compound of the formula 1, prepared according to an embodiment of the present invention.
Figure 8:
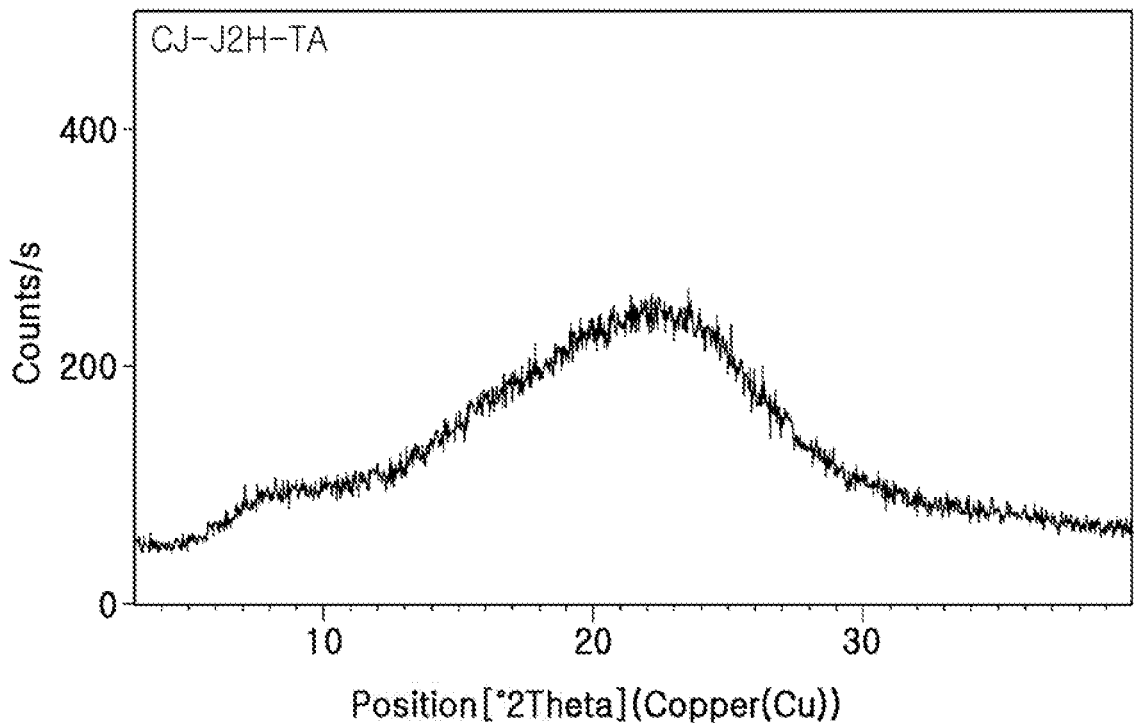
FIG. 8 shows a PXRD results of a tartaric acid salt of an amorphous compound of the formula 1, prepared according to an embodiment of the present invention.

A 100 g of a crystalline compound of a formula 1 and 36.33 g of L-malic acid (1.05 eq.) were completely dissolved in 1000 ml of methanol at 25° C., and then a resulting solution was concentrated at 50° C. while being stirred under decompression until a solid was precipitated. A co-solvent of acetone and ethyl acetate was added to a concentrate at 25° C. at a ratio of acetone:ethyl acetate=1:4 (500 ml), and a resulting solution was stirred agitatedly for 30 minutes. The solid was filtered out under decompression, washed with 100 ml of ethyl acetate, and vacuum-dried at 40° C. for 16 hours, such that a malate salt of an amorphous compound of the formula 1 was obtained by 120.4 g (yield 89.4%) in a form of white powder (FIG. 2).

Comparative Example 1: Preparing of an Amorphous Free Base of a Compound of a Formula 1

A 100 g of a compound of a formula 1 was completely dissolved in 1000 ml of methanol at 25° C., and then a resulting solution was concentrated at 50° C. while being stirred under decompression until a solid was precipitated. A co-solvent of acetone and ethyl acetate was added to a concentrate at 25° C. at a ratio of acetone:ethyl acetate=1:4 (500 ml), and a resulting solution was stirred agitatedly for 30 minutes. The solid was filtered out under decompression, washed with 100 ml of ethyl acetate, and vacuum-dried at 40° C. for 16 hours, such that a free base of an amorphous compound of the formula 1 was obtained by 94.7 g (yield 94.7%) in a form of white powder.

Experimental Example 1: Comparative Test on Solubility

Amorphous acid addition salts were prepared after 12 acids were selected as shown in a table 3 so that an anion could not act as a nucleophile after the compound was protonated/acidificated by means of acid addition salts, while enhancing a solubility of a compound of the formula 1.

TABLE 3

| No. | Types of acid for preparing acid addition salts |
|---|---|
| 1 | Succinic acid |
| 2 | Fumaric acid |
| 3 | Oxalic acid |
| 4 | Citric acid |
| 5 | L-pyroglutamic acid |
| 6 | 1.5-naphinalene disulfonic acid |
| 7 | p-toluenesulfonic acid |
| 8 | Benzene sulfonic acid |
| 9 | L-malic acid |
| 10 | Nicotinic acid |
| 11 | 2.5-dihydroxybenzoic acid |
| 12 | L-tartaric acid |

Specifically, in case of 11 acids excluding 1.5-naphthalene disulfonic acid, acid addition salts were prepared in such a way that an equivalent weight thereof was at a molar ratio of 1:1 between each of the acids and a compound of the formula 1. In case of 1.5-naphthalene disulfonic acid, a hemi-salt was prepared in such a way that an equivalent weight thereof was at a molar ratio of 0.5:1 between this acid and a compound of the formula 1. The above-mentioned preparing method was the same as in Examples 1 and 2.

A following table 4 indicates a water solubility of the 12 amorphous acid addition salts at a room temperature. Each of water solubility was measured by means of a supersaturation method. Each solubility was not converted based on a free base of the formula 1, but a solubility of acid addition salts per se was measured, wherein results thereof were indicated in a following table 4. Also, a solubility of an amorphous free base of the compound of the formula 1 in the comparative example 1 was measured, wherein results thereof were indicated in a following table 4.

TABLE 4

| No. | Types of acid used in preparing of acid addition salts of the compound of the formula 1 | Water solubility (mg/ml) |
|---|---|---|
| 1 | Succinic acid | 15 |
| 2 | Fumaric acid | 52 |
| 3 | Oxalic acid | >100 |
| 4 | Citric acid | 55 |
| 5 | L-pyroglutamic acid | >100 |
| 6 | 1.5-naphinalenedisulfonic acid | 2.5 |
| 7 | p-toluenesulfonic acid | 27 |
| 8 | Benzene sulfonic acid | 22 |
| 9 | L-malic acid | >100 |
| 10 | Nicotinic acid | 5 |
| 11 | 2.5-dihydroxybenzoic acid | 20 |
| 12 | L-tartaric acid | 58 |
| 13 | Amorphous free base of the compound of the formula 1 | 3 |

As seen in the table 4, it was identified that out of 12 acid addition salts, six types of salt indicated a water solubility of 50 mg/ml or more. Specifically, fumaric, oxalic, citric, L-pyroglutamic, L-malic and L-tartaric acid salts exhibited an effect on improving solubility. In particular, it was also identified that oxalic, L-pyroglutamic and L-malic acid salts exhibited a remarkably excellent solubility of 100 mg/ml or more.

Based on the above-mentioned results, it could be seen that amorphous acid addition salts of the compound of the formula 1 had solubility greatly increased compared to an amorphous free base, in particular showing a different effect on improving solubility depending on salt types.

Experimental Example 2: X-Ray Powder Diffraction (PXRD) Analysis

A PXRD analysis was performed to analyze crystalline changes of the compound of the formula 1 present in a salt of the compound of the formula 1.

Specifically, six types of amorphous acid-addition salt (L-pyroglutamic, fumaric, oxalic, citric, L-malic and L-tartaric acid salts) of a compound of the formula 1, having a water solubility of 50 mg/ml or more, as identified in the above-mentioned experimental example 1, were respectively inserted into each PE-bag and then the resulting bags were stored inside a stable chamber with the condition of 40° C. and 75% RH for one month. After then, a Cu—Kα line was used on an X-ray powder diffractometer (D8 Advance) to perform a PXRD analysis of the salts. The diffractometer was equipped with penetration and a current capacity was set to 45 kV and 40 mA. A divergence and scattering slit was set to 1° and a receiving slit was set to 0.2 mm. A θ-2θ continuous scan of 3°/minute (0.4 second/0.02° interval) was used from 5 to 35° 2θ.

As a result of checking PXRD in one month after storage, it was identified that all types of salt maintained to be amorphous, thereby having no crystal transition observed (FIGS. 3 to 8).

Experimental Example 3: Comparative Test on Liquid-Phase Stability

Six types of amorphous acid addition salt (L-pyroglutamic, fumaric, oxalic, citric, L-malic and L-tartaric acid salts) of the compound of the formula 1, having a water solubility of 50 mg/ml or more, as identified in the experimental example 1, were respectively dissolved in purified water to be prepared at a concentration of 20 mg/ml, and then a resulting solution was stirred at 40° C., such that the solution was analyzed with an HPLC in an initial stage and on a first day. Accordingly, a generation amount of degradation products (a compound of a formula 4) was converted into a percentage (%) compared to an area under the curve (AUC) of the compound of the formula 1 in a diluent state without a polymorphism, wherein results thereof were indicated in a following table 5.

TABLE 5

| | Commtration (%) of degradation product (compound of the formula 4) | |
|---|---|---|
| Add addition salts | Initial | 1 day (24 hours) elapsed |
| Fumaric acid | — | 0.20 |
| Oxalic acid | 0.10 | 0.57 |
| Citric acid | — | 0.27 |
| L-pyroglutamic acid | 0.02 | 0.05 |
| L-malic acid | 0.03 | 0.07 |
| L-tartaric acid | 0.06 | 0.21 |

In result, it was identified that L-pyroglutamic and L-malic acid salts of the compound of the formula 1 had liquid-phase stability at least three times more excellent than other salts and a degradation product represented by the formula 4 compound was generated most in an oxalic acid salt of the compound of the formula 1. Therefore, in view of ICH guidelines on active pharmaceutical ingredients (API) of an injection formulation, in which degradation products must be managed to be 0.1% or less, it was identified that salts of L-pyroglutamic and L-malic acid salts only were pharmaceutically available and stable acid addition salts.

Meanwhile, in terms of physical properties, it was identified that citric and fumaric acid salts formed a sticky gel not to maintain a homogenous liquid-phase state, while the rest of four salts maintained a homogenous liquid-phase state.

Experimental Example 4: Comparative Test on Solid-Phase Stability

Six types of amorphous acid-addition salt (L-pyroglutamic, fumaric, oxalic, citric, L-malic and L-tartaric acid salts) of a compound of the formula 1, having a water solubility of so mg/ml or more, as identified in the above-mentioned experiment 1, were respectively inserted into each PE-bag and then the resulting bags were stored inside a stable chamber with the condition of 40° C. and 75% RH for one month. Then, the generation amounts of water checked through Karl Fischer analysis, of impurity checked through HPLC analysis, and of degradation product (a compound of Formula 4) measured under the conditions identical to the experimental example 3, were respectively converted into an area percentage, wherein results thereof were indicated in a following table 6.

TABLE 6

| | Moisture (%) | | Concentration of degradation products (%) | | Total impurities (%) | |
|---|---|---|---|---|---|---|
| Acid addition salts | Initial | 1 month elapsed | Initial | 1 month elapsed | Initial | 1 month elapsed |
| Fumaric acid | 0.1 | 0.3 | 0.09 | 0.12 | 0.14 | 0.43 |
| Oxalic acid | 0.4 | 0.4 | 0.11 | 0.19 | 0.16 | 0.80 |
| Citric acid | 0.2 | 0.2 | 0.09 | 0.17 | 0.12 | 0.27 |
| L-pyroglutamic acid | 0.1 | 0.1 | 0.02 | 0.02 | 0.07 | 0.07 |
| L-malic acid | 0.1 | 0.1 | 0.04 | 0.04 | 0.06 | 0.06 |
| L-tartaric acid | 0.6 | 0.7 | 0.10 | 0.18 | 0.15 | 0.26 |

In result, similarly to results of liquid-phase stability, a solid-phase accelerated stability was most excellent in L-pyroglutamic and L-malic acid salts of the compound of the formula 1, and a total amount of impurities was most in the fumaric acid salt. Therefore, in view of ICH guidelines on active pharmaceutical ingredients (API) of an injection formulation, in which impurities must be managed to be 0.1% or less, it was identified that L-pyroglutamic and L-malic acid salts only were pharmaceutically available and stable acid addition salts.

Meanwhile, in terms of physical properties, hygroscopicity was not observed in all types of salt and it was identified with naked eyes that a white powder type was maintained therein.

Experimental Example 5: Comparative Test on Precipitation Stability

Six types of amorphous acid-addition salt (L-pyroglutamic, fumaric, oxalic, citric, L-malic and L-tartaric acid salts) of a compound of the formula 1, having a water solubility of 50 mg/ml or more, as identified in the experimental example 1, were completely dissolved in a buffer solution of pH 6.8 at a concentration of 10 mg/ml respectively and stored at 37° C. for a 24 hours. After that, states of such solutions were observed, wherein results thereof were indicated in a following table 7.

TABLE 7

| Acid addition salts | Soil precipitation or not |
|---|---|
| Fumaric acid | Precipitated |
| Oxalic acid | Precipitated |
| Citric acid | Precipitated |
| L-pyroglutamic acid | Homogenous solution maintained |
| L-malic acid | Homogenous solution maintained |
| L-tartaric acid | Homogenous solution maintained |

In result, it was identified that a solid was precipitated in fumaric, oxalic and citric acid salts, while a homogenous solution was maintained in L-pyroglutamic, L-malic and L-tartaric acid salts. Accordingly, it was identified that L-pyroglutamic, L-malic and L-tartaric acid salts have excellent precipitation stability.

Experimental Example 6: Temperature Differential Scanning Calorimetry (DSC) Analysis DSC Q20, available from TA Company, was used to carry out a DSC measurement in an enclosed fan at a scanning speed of 10° C./min from 20 to 300° C. under nitrogen purification. Specifically, a DSC measurement was performed on a crystalline compound of the formula 1, which is a reactant of the examples 1 and 2, as well as an amorphous pidolate salt and malate salt, which are products.

Figure 9:
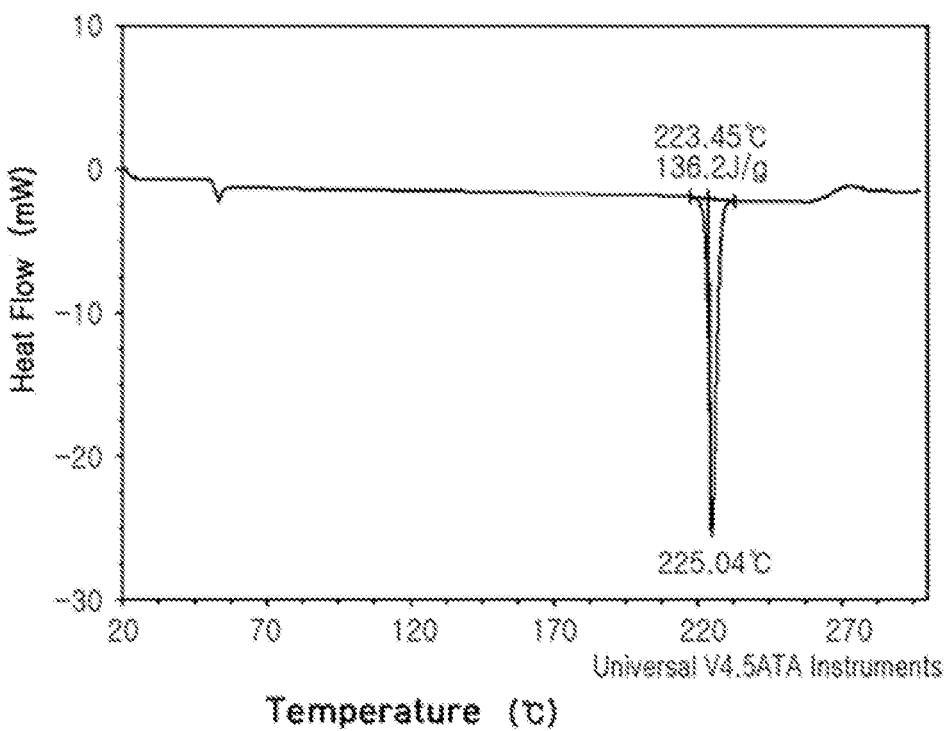
FIG. 9 shows a DSC results of a free base of a crystalline compound of the formula 1.
Figure 10:
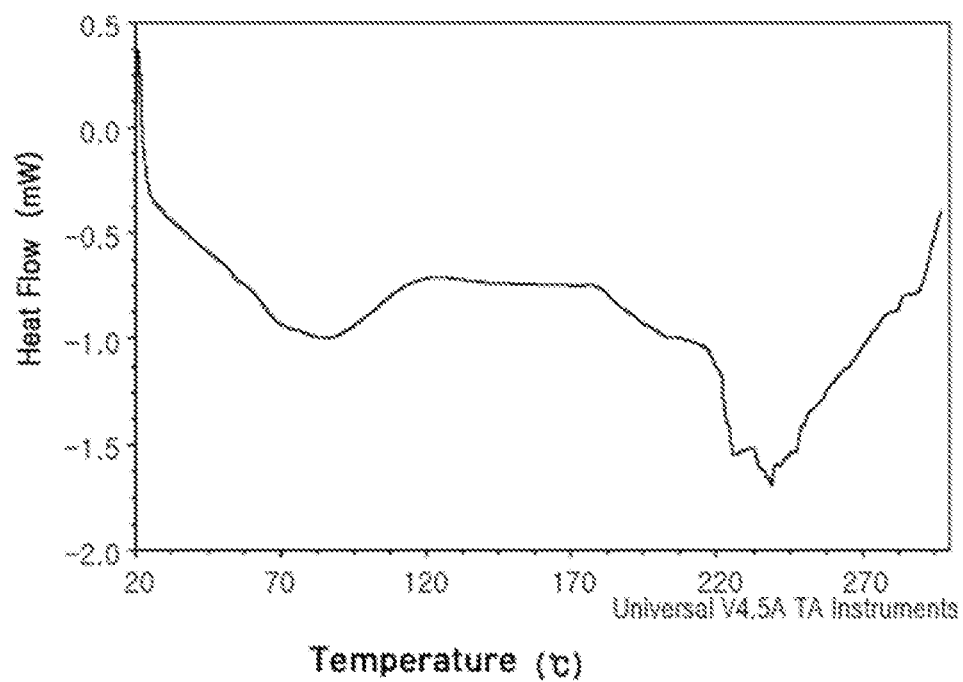
FIG. 10 shows a DSC results of a pidolate salt of an amorphous compound of the formula 1, prepared according to an embodiment of the present invention.
Figure 11:
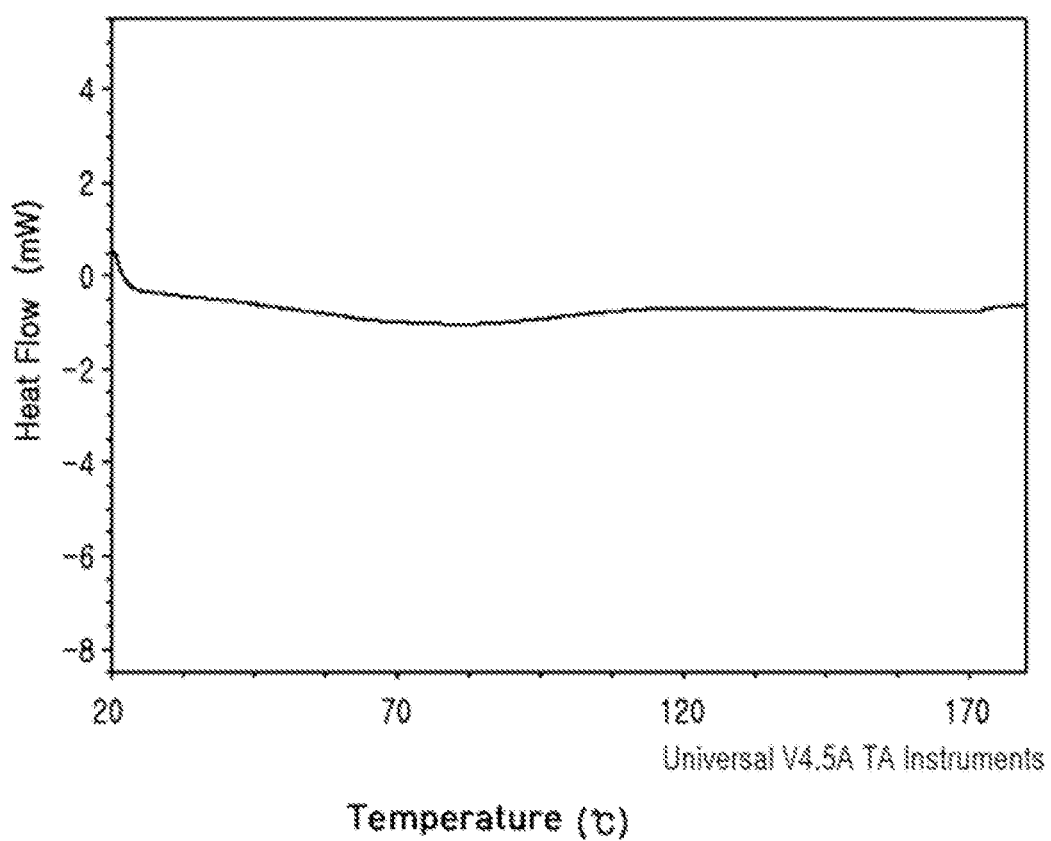
FIG. 11 shows a DSC results of a malate salt of an amorphous compound of the formula 1, prepared according to an embodiment of the present invention.

In result, it was identified that amorphous acid addition salts (pidolate and malate salts) were synthesized from a free base of a crystalline compound of the formula 1 (FIGS. 9 to 11)

According to the above-mentioned results, it was identified that the pidolate of the compound of the formula 1 represented by the formula 2 as well as the malate salt of the compound of the formula 1 represented by the formula 3 were pharmaceutical ingredients for injection preparation, which are optimized for a benzimidazole derivative of the formula 1.

While specific parts of the present invention have been described in detail above, it is apparent to those skilled in the art that such detailed description are just exemplary embodiments, but are not to be construed to limit a scope of the present invention.

Accordingly, the substantial scope of the present invention will be defined based on accompanying claims and equivalents thereof.

The detailed descriptions about the contents that can be readily understood and inferred by those skilled in the art were omitted herein. In addition to detailed examples described in the present specification, various modifications are possible without departing from the technical idea or essential features of the present invention. Therefore, the present invention can be implemented in other ways than concretely described and illustrated in the present specification, and this is readily understood by those skilled in the art.

The invention claimed is:
1. A pidolate salt of a compound represented by Formula 1, prepared by a process comprising:
   a) dissolving a compound represented by Formula 1 and pyroglutamic acid in an organic solvent, thereby creating a solution;
   b) concentrating the solution under decompression to precipitate a solid, then adding a co-solvent and stirring; and
   c) filtering out and drying the precipitated solid:

[Formula 1]

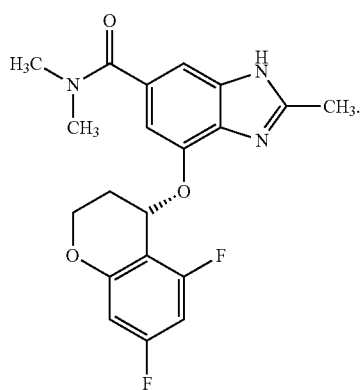

2. The method of 1, wherein the organic solvent is added in a volume 5 to 20 times (volume/weight) compared to the amount of compound represented by Formula 1.

3. The method of claim 1, wherein the organic solvent is methanol.

4. The method of claim 3, wherein the methanol is added in a volume 5 to 20 times (volume/weight) compared to the amount of compound represented by Formula 1.

5. The method of claim 4, wherein the methanol is added in a volume 10 times (volume/weight) compared to the amount of compound represented by Formula 1.

6. The method of claim 1, wherein the co-solvent is a mixed solution of acetone and ethyl acetate.

7. The method of claim 6, wherein the ratio of acetone to ethyl acetate is 1:4 (v/v).

8. The method of claim 6, wherein the mixed solution of acetone and ethyl acetate is added in a volume 5 to 20 times (volume/weight) compared to the amount of compound represented by Formula 1.

9. The method of claim 8, wherein the mixed solution of acetone and ethyl acetate is added in a volume 5 times (volume/weight) compared to the amount of compound represented by Formula 1.

10. The method of claim 1, wherein the pyroglutamic acid is L-pyroglutamic acid.

11. A malate salt of a compound represented by Formula 1, prepared by a process comprising:
    a) dissolving a compound represented by Formula 1 and malic acid in an organic solvent, thereby creating a solution;
    b) concentrating the solution under decompression to precipitate a solid, then adding a co-solvent and stirring; and
    c) filtering out and drying the precipitated solid:

[Formula 1]

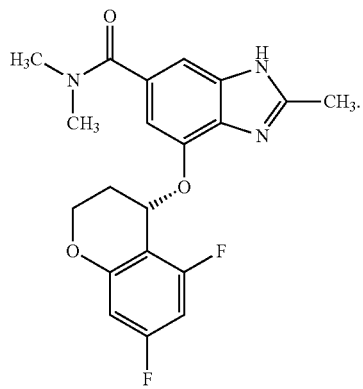

12. The method of 11, wherein the organic solvent is added in a volume 5 to 20 times (volume/weight) compared to the amount of compound represented by Formula 1.

13. The method of claim 11, wherein the organic solvent is methanol.

14. The method of claim 13, wherein the methanol is added in a volume 5 to 20 times (volume/weight) compared to the amount of compound represented by Formula 1.

15. The method of claim 14, wherein the methanol is added in a volume 10 times (volume/weight) compared to the amount of compound represented by Formula 1.

16. The method of claim 11, wherein the co-solvent is a mixed solution of acetone and ethyl acetate.

17. The method of claim 16, wherein the ratio of acetone to ethyl acetate is 1:4 (v/v).

18. The method of claim 16, wherein the mixed solution of acetone and ethyl acetate is added in a volume 5 to 20 times (volume/weight) compared to the amount of compound represented by Formula 1.

19. The method of claim 18, wherein the mixed solution of acetone and ethyl acetate is added in a volume 5 times (volume/weight) compared to the amount of compound represented by Formula 1.

20. The method of claim 11, wherein the malic acid is L-malic acid.

* * * * *